United States Patent [19]

SinghDeo et al.

[11] Patent Number: 5,024,883
[45] Date of Patent: Jun. 18, 1991

[54] ELECTRONIC PACKAGING OF COMPONENTS INCORPORATING A CERAMIC-GLASS-METAL COMPOSITE

[75] Inventors: Narendra N. SinghDeo, New Haven; Deepak Mahulikar, Meriden, both of Conn.; Sheldon H. Butt, Godfrey, Ill.

[73] Assignee: Olin Corporation, New Haven, Conn.

[21] Appl. No.: 407,511

[22] Filed: Sep. 14, 1989

Related U.S. Application Data

[62] Division of Ser. No. 924,970, Oct. 30, 1986, Pat. No. 4,882,212.

[51] Int. Cl.$^5$ ............................................. B32B 9/00
[52] U.S. Cl. ............................ 428/323; 428/328; 428/426; 428/428; 428/432; 428/433; 428/688; 428/901; 361/403; 361/411; 156/85
[58] Field of Search ........................... 501/32, 76; 75/232–235; 428/426, 323, 428, 328, 432, 433, 688, 901; 361/403, 411; 156/89

[56] References Cited

U.S. PATENT DOCUMENTS

| | | | |
|---|---|---|---|
| 3,781,457 | 12/1973 | McKerreghan | 174/525 |
| 4,002,799 | 1/1977 | Dumesnil et al. | 428/428 |
| 4,186,023 | 1/1980 | Dumesnil et al. | 106/53 |
| 4,293,325 | 10/1981 | Chirino et al. | 65/43 |
| 4,299,887 | 11/1981 | Howell | 428/428 |
| 4,491,622 | 1/1985 | Butt | 428/632 |
| 4,532,222 | 7/1985 | Butt | 501/32 |
| 4,569,692 | 2/1986 | Butt | 75/235 |
| 4,598,167 | 7/1986 | Ushifusa et al. | 174/68.5 |
| 4,622,433 | 11/1986 | Frampton | 174/52 FP |
| 4,657,699 | 4/1987 | Nair | 252/513 |
| 4,659,404 | 4/1987 | Butt | 156/62.2 |
| 4,682,414 | 7/1987 | Butt | 29/840 |
| 4,696,851 | 9/1987 | Pryor | 361/411 |
| 4,712,161 | 12/1987 | Pryor | 361/403 |
| 4,715,892 | 12/1987 | Mahulikar | 75/233 |
| 4,725,333 | 2/1988 | Ledeke et al. | 156/630 |
| 4,743,299 | 5/1988 | Pryor et al. | 75/235 |
| 4,748,136 | 5/1988 | Mahulikar et al. | 501/32 |
| 4,761,518 | 8/1988 | Butt et al. | 174/52 FP |
| 4,771,537 | 9/1988 | Pryor et al. | 29/830 |
| 4,821,151 | 4/1989 | Pryor et al. | 361/403 |
| 4,882,212 | 11/1989 | SinghDeo et al. | 428/76 |

Primary Examiner—Patrick J. Ryan
Attorney, Agent, or Firm—Gregory S. Rosenblatt; Paul Weinstein

[57] ABSTRACT

The present invention is directed to components and the process of forming the components for housing semiconductor devices. The components are formed of a unique ceramic-glass-metal composite material comprising ceramic particles, metallic particles and a glass matrix with said ceramic and metallic particles dispersed throughout. Metal elements can be embedded into the material to enable simplified fabrication of devices such as semiconductor packaging.

22 Claims, 3 Drawing Sheets

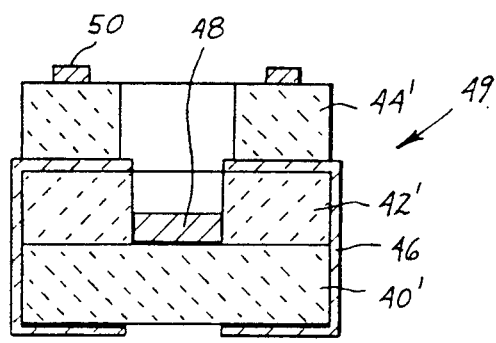
FIG-8
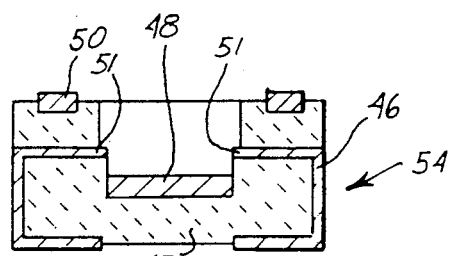
FIG-9
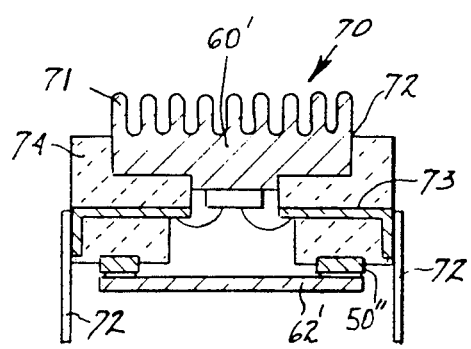
FIG-11
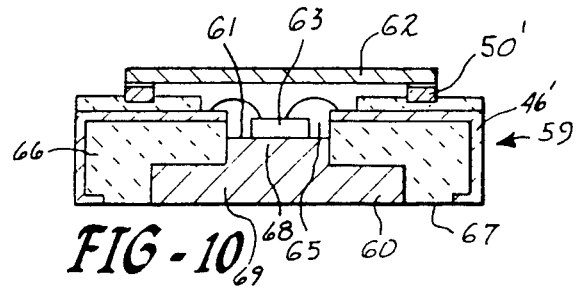
FIG-10
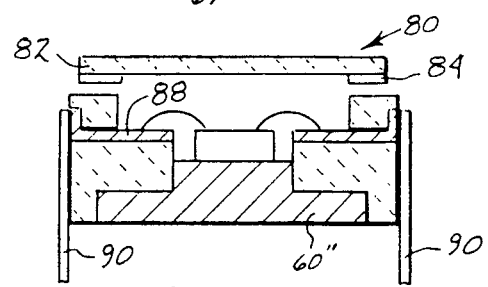
FIG-12
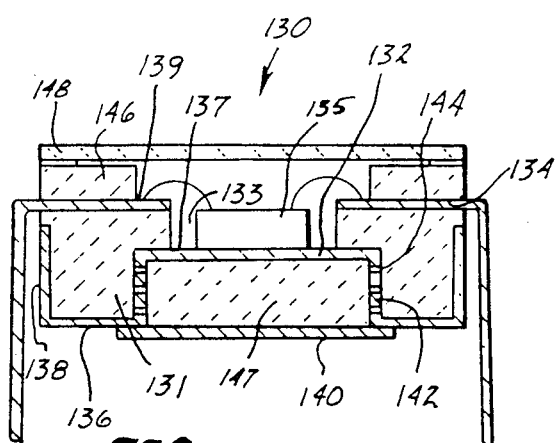
FIG-15
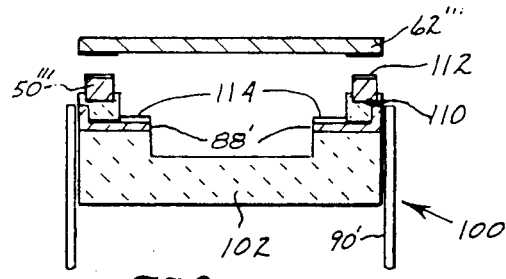
FIG-13
FIG-3B
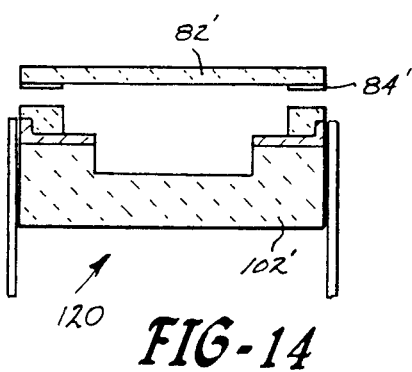
FIG-14 ered in accordance with
ELECTRONIC PACKAGING OF COMPONENTS INCORPORATING A CERAMIC-GLASS-METAL COMPOSITE This application is a division of Ser. No. 06/924,970, filed Oct. 30, 1986, U.S. Pat. No. 4,882,212.

While the invention is subject to a wide range of applications, it is especially suited for use as a fabricating component for semiconductor chips individually or in groups. The invention discloses the bonding together of ceramic particles to form a coherent composite with desired properties which may be specfically tailored for specific applications in the packaging of electronic components.

This application relates to U.S. Pat. No. 4,569,692, entitled LOW THERMAL EXPANSIVITY AND HIGH THERMAL CONDUCTIVITY SUBSTRATE, by S. H. Butt; U.S. Pat. No. 4,715,892, entitled CERMET SUBSTRATE WITH GLASS ADHESION COMPONENT, by D. Mahulikar; U.S. Pat. No. 4,743,229 entitled CERMET SUBSTRATE WITH SPINEL ADHESION, by M. J. Pryor et al.; U.S. Pat. No. 4,748,136, entitled CERAMIC-GLASS-METAL COMPOSITE by N. N. SinghDeo et al.; U.S. Pat. No. 4,883,778, entitled PRODUCTS FORMED OF CERAMIC-GLASS-METAL COMPOSITES, by N. N. SinghDeo et al.; U.S. patent application Ser. No. 707,636, entitled PIN GRID ARRAY, by M. J. Pryor (now abandoned);

U.S. Pat. No. 4,827,377 entitled "MULTI-LAYER CIRCUITRY" by Sheldon H. Butt; U.S. Pat. No. 4,775,647, entitled "SEALING GLASS COMPOSITE" by Edward F. Smith, III; U.S. Pat. No. 4,752,521 entitled "SEALING GLASS COMPOSITE" by Edward F. Smith, III et al.; U.S. patent application Ser. No. 811,908 (now abandoned), entitled "STEEL SUBSTRATE WITH BONDED FOIL" by Richard A. Eppler; U.S. Pat. No. 4,712,161, entitled "HYBRID AND MULTI-LAYER CIRCUITRY" by Michael J. Pryor et al.; U.S. Pat. No. 4,821,151, entitled "A HERMETICALLY SEALED PACKAGE" by Michael J. Pryor et al.; U.S. Pat. No. 4,771,537, entitled "A METHOD OF JOINING METALLIC COMPONENTS" by Michael J. Pryor et al.; U.S. Pat. No. 4,696,851, entitled "HYBRID AND MULTI-LAYER CIRCUITRY" by Michael J. Pryor et al.; U.S. Pat. No. 4,840,654, entitled "MULTI-LAYER AND PIN GRID ARRAYS" by Michael J. Pryor; U.S. Pat. No. 4,491,622, entitled "COMPOSITES OF GLASS-CERAMIC TO METAL SEALS AND METHOD OF MAKING THE SAME" by Sheldon H. Butt; and U.S. Pat. No. 4,725,333, entitled "METAL-GLASS LAMINATE" by Charles J. Leedecke et al.

In the past, glass-ceramic composites have been formed by one-step processes into complex shapes as described in U.S. Pat. No. 4,840,654. This technique proved effective for many applications. However, as the final product had a more complex shape, the higher pressure required to form the composite within the mold resulted in the molten glass between the ceramic particles being squeezed out and interlocking of ceramic particles. The result is a retardation of further flow so that the densification and shaping of the composite to the desired final configuration requires more pressure or may not be possible. The present invention overcomes this problem by combining metallic particles with the ceramic particles and glass to enhance the flow of the composite within the mold.

The composite may be formed of a combination of materials such that it is either electrically conductive or non-electrically conductive. Also, the coefficient of thermal expansion may be regulated in accordance with the requirements of the specific application.

A composite having a low coefficient of thermal expansion, while being non-electrically conductive, is particularly useful in the electronics industry. Presently, low expansivity materials are widely used in the microelectronic industry as substrate materials for semiconductor packages, hybrid circuit packages and chip carriers. These materials are particularly useful when the coefficient of thermal expansion (CTE) of the substrate is critical, i.e. when silicon chips or low expansivity leadless chip carriers are mounted directly to the substrate.

Alumina ceramics are presently the most widely used substrate material. There is a moderate mismatch between the coefficients of thermal expansion of alumina and the silicon chip. This mismatch does not usually generate unacceptably high stresses on a chip mounted to an alumina substrate when they are subjected to thermal cycling. This degree of CTE mismatch is usually acceptable even when the chip sizes are relatively large or when the chip is rigidly adhered to the substrate. Alumina ceramics are particularly attractive since they are less costly than most other low expansivity substrate materials. However, there are a number of drawbacks to alumina ceramics made in the conventional way such as poor tolerance control, poor thermal conductivity, i.e. in the range of about 10 to about 20 watts per meter kelvin, and manufacturing capabilities limiting alumina substrate areas to less than about 50 sq. in.

Conventional ceramic products, and ceramic substrates in particular, may be manufactured in accordance with the following procedure. Powders of alumina or other ceramic materials are mixed together with glass powders and organics. In the conventional "green tape" or "cold press" processes, the organics are two phase mixtures consisting of a solvent, such as terpineol, and a solute, such as polymethylmethacrylate. This particular solvent-solute mixture is exemplary and other organic mixtures may be used in their place. The organic mixture forms a paste or slurry when mixed with the mixture of glass and ceramic powders. The solute:solvent ratio and the type of organic mixture, is selected in accordance with the paste rheology desired for the particular application, i.e. the "green tape" or the "cold press" process.

In the green tape process, a controlled amount of slurry is placed between two sheets of plastic. The slurry, sandwiched between the plastic sheets, is passed through a rolling mill to attain a consistent thickness. The sheets of material are then cut or punched into desired shapes for firing. In the cold press process, the glass and ceramic powders are mixed with a lower percentage of solvent, as compared with the green tape process. The mixture of glass, ceramic and organics is then pressed into a desired shape and fired.

The organics, in either process, are volatilized at substantially lower temperatures than the firing or processing temperature of the ceramic bodies or ceramic substrates. The solvents usually evaporate at temperatures below about 100° C. and the solutes evaporate at temperatures below about 450° C. The loss of the solute and solvent leaves pores in the green tape or cold pressed body. At the peak firing temperatures (approximately 1600° C. for the conventional ceramics or approximately 900° C. for the low fired ceramics), the glassy phase melts, a certain amount of sintering of the alumina particles occurs, and there is a resulting densification of the bodies. The fired substrates, being devoid of any connected pores, produce a hermetic substrate that allows an extremely limited quantity of gaseous penetration ($<1\times10^{-8}$ cc He/sec). The latter characteristics of the fired substrates make them particularly suitable for fabricating hermetically sealed, semiconductor enclosures.

The densification, however, causes a great deal of shrinkage, amounting to as much as 17% in the linear dimension. It is thus unrealistic to economically produce finished parts which have better than about ±1% tolerance in the linear dimension. Therefore, dimensional tolerances for the standard fired ceramic substrates is typically quoted by ceramic manufacturers to be ±1%. Tighter dimensional tolerances are considerably more expensive so as to offset the yield loss.

The electronic industry is seeking higher levels of automation in their factories. The automatic machines are generally capable of positioning parts, such as the previously described substrates, to a much tighter tolerance than ±1% of the linear dimension of the part. In fact, the tolerance of the ceramic part is, in most cases, the limiting factor in attaining the desired level of automation.

The present invention provides a unique method of manufacturing structures of ceramic-glass-metal to their final configuration in a one-step process by conventional means at temperatures well below the firing temperature of either the conventional ceramics, i.e. about 1600° C., or even "low fired ceramics", i.e. about 900° C. The present process also imparts unique properties to the manufactured product because organics are not necessarily required in the manufacturing process.

The present invention is also directed to components and methods of producing components for radically improving the CERDIP technology. Currently, the CERDIP technology utilizes a ceramic base and lid. A sealant, usually a solder glass, seals the package at a relatively low temperature, i.e. about 470° C. A metallic leadframe resides in the sealant. The strength of the CERDIP seal depends on the strength of the glass sealant, the length and width of the seal, the presence of pores or other discontinuities and eventually the nature of the bond between the glass and the metallic leadframe. Usually, the glass is the weakest component of the CERDIP package. The adhesion between the leadframe and the glass sealant is relatively poor in most package designs. If the seals are subjected to significant mechanical or thermo-mechanical loading, the seal can readily fail. Under similar conditions, a more expensive, ceramic side brazed package, utilizing a metallic seal, would remain intact.

The CERDIP designs are modified to compensate for their inherent weakness. They have a larger seal area as compared to a side brazed package of the same size. The result is a die cavity of reduced width as compared with that of the side brazed package. In instances where the size of the space to accomodate the package is limited, larger chips which cannot be fit within the reduced sized die cavity of a CERDIP, require mounting in a more expensive side brazed ceramic package. The present invention can overcome this problem by separating the leadframe from the interior of the glass seal. The leadframe can be firmly affixed to the base or lid of the package in the manner of the side brazed package. The resulting superior package does not transmit stress into the seal from flexure of the leads which routinely occurs during the handling of the package. At the same time, the size of the die cavity may be enlarged so that the package competes in reliability with the sidebrazed package but at a much lower cost.

The present invention is also suitable for fabricating multi-layer packages, such as pin grid arrays and side-brazed packages as disclosed in U.S. Pat. No. 4,840,654.

It is a problem underlying the present invention to manufacture electronic packaging for components incorporating a ceramic-glass-metal composite whose physical characteristics can be tailored to provide specific mechanical, electrical, thermal, and chemical properties by judicious choice.

It is an advantage of the present invention to provide electronic packaging for components incorporating a composite and a method of forming the composite which obviates one or more of the limitations and disadvantages of the described prior arrangements.

It is a further advantage of the present invention to provide electronic packaging for components incorporating a composite and a method of forming the composite which provides a substrate having good flexure strength.

It is a still further advantage of the present invention to provide electronic packaging for components incorporating a composite and a method of forming the composite which can produce parts with a tight tolerance.

It is another advantage of the present invention to provide electronic packaging for components incorporating a composite and a method of forming the composite which can be fired at a low temperature.

It is yet another advantage of the present invention to provide electronic packaging for components incorporating a composite and a method of forming the composite which can be inexpensively processed.

It is a still further advantage of the present invention to embed a metallic element into a component formed of a ceramic-metal-glass composite.

It is a yet further advantage of the present invention to provide electronic packaging for components incorporating a leadframe embedded into a ceramic substrate formed of a ceramic-metal-glass composite.

It is still another advantage of the present invention to provide electronic packaging for components incorporating a multi-layer device fabricated from a ceramic-glass-metal composite having metallic elements embedded into the composite at desired locations.

Accordingly, there has been provided components and the process of forming the components for housing semiconductor devices. The components are formed of a unique ceramic-glass-metal composite material comprising ceramic particles, metallic particles dispersed throughout the composite and a glassy phase for adhering the ceramic and metallic particles together. The composite may be formed, in a single step, by conventional processes such as hot forging and hot pressing in a mold to enable simplified fabrication of semiconductor packaging. Metallic elements can be embedded into the composite during the hot pressing step. The invention is particularly adaptable to form CERDIP's, hybrid packages, circuit boards and multilayer devices.

The invention and further developments of the invention are now elucidated by means of the preferred embodiments in the drawings.

Detailed Description of the Drawings

FIG. 3B illustrates a cross-sectional view through the ceramic-glass-metal substrate of FIG. 3A having the leadframe embedded therein.

FIG. 8 illustrates the components of a multilayer device prior to hot pressing.

FIG. 9 illustrates the components of a multilayer device subsequent to hot pressing.

FIG. 10 illustrates a semiconductor casing including a heat sink.

FIG. 11 illustrates a semiconductor casing formed of a ceramic-glass-metal composite in accordance with the present invention.

FIG. 12 illustrates a semiconductor casing of a ceramic-glass-metal composite including a ceramic lid.

FIG. 13 illustrates a semiconductor casing formed of a ceramic-glass-metal composite and including a metal lid.

FIG. 14 illustrates a semiconductor device similar to the embodiment of FIG. 12 but without a heat sink.

FIG. 15 illustrates a semiconductor casing formed of a body of the ceramic-glass-metal composite and including a cup shape member which acts as a surface to bond the semiconductor device to as well as a heat sink.

Figure 1:
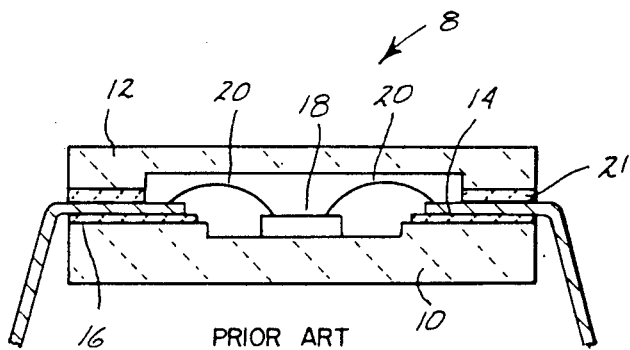
FIG. 1 illustrates a prior art CERDIP package.

The present invention particularly relates to a composite formed of a mixture of ceramic and metal particles bound together by a glass. The composite can be formed into any desired shape by techniques such as hot forging and hot pressing at a processing temperature where the selected glass is at least soft and preferably in the fluid condition. The resulting shaped composite is particularly adaptable, for example, to form substrates for semiconductor devices, hybrid packages, multilayer packages or rigid, printed circuit boards.

The invention involves mixing together appropriate proportions of at least three different types of materials to provide selected properties. One of the materials is a ceramic powder which is present in a volume percent range selected according to the desired physical property requirements such as the mechanical, electrical, thermal and chemical properties. Typically, ceramics are known for their physical characteristics including high strength, low ductility, high dielectric constant, low coefficient of thermal expansion and chemical nonreactivity. The second material is a glass which forms a matrix for binding the ceramic and metallic particles together. Since glass is relatively fragile, it is typically provided at such a proportion so as to prevent a significant reduction of the composite strength, primarily provided by the ceramic particles. The glass is selected to be chemically reactive with the ceramic particles as well as with the third material, metal or alloy particles. The third material is comprised of metal or alloy particles which are dispersed throughout the composite. The metal or alloy particles enable the ceramic particles to shift position, while the composite is being pressed into a desired shape at the processing temperature, with less applied pressure as compared to a ceramic-glass slurry alone. In addition, the metal particles improve the thermal conductivity of the composite. The metal particles are preferably soft and ductile. It is believed that they tend to mold onto the adjacently disposed surfaces between adjacent ceramic particles so that the ceramic particles can slide over each other during the forming process without being damaged. It is believed that the metal particles substantially reduce the occurrence of interlocking between ceramic particles thereby reducing the pressure necessary for forming the final shapes. The resulting composite is particularly useful in that it may be readily formed by a one step process into a complex, final shape having a very tight tolerance.

The ceramic material typically comprises particles selected for their physical characteristics. The specific ceramic may be selected from the group consisting of $Al_2O_3$, $SiC$, $BeO$, $TiO_2$, $ZrO_2$, $MgO$, $AlN$, $Si_3N_4$, $BN$ and mixtures thereof. The present invention is not limited to these ceramics and may incorporate any desired ceramic or mixture of ceramics. The ceramic particles are present in a range of from about 20 to about 80 volume percent of the final fired composite and in a preferred range of from about 40 to about 65 volume percent. The ceramic particles can have any desired shape and have an average diameter of over about 1 micron, preferably, between about 1 to about 200 microns and most preferably, between about 40 to about 100 microns. The factors considered in selecting the desired ceramic include its dielectric constant, its coefficient of thermal expansion, its strength and chemical durability.

Conventionally, ceramics have been chosen for their high temperature capabilities since their melting point is at a temperature between about 1300° to about 2500° C. However, the present invention may not require the high temperature capabilities since the ceramic particles are bonded together in a glassy matrix which may have a relatively low softening temperature as compared to that of the ceramic. It is also within the terms of present invention to choose glasses which can be frabricated into components that are stable at very high temperatures.

A second component of the composite comprises a glassy phase having any desired composition in accordance with the properties required by the final composite. The glassy phase functions to bind the ceramic and metallic particles together within a matrix of the glass. An important characteristic is that the glass preferably is chemically reactive with both the ceramic and metallic particles. Also, it may be important that the glass has physical characteristics such as good chemical durability, high strength, an acceptable dielectric constant, and a softening point in a selected temperature range. Suitable glasses may be selected from the group consisting of silicate, borosilicate, phosphate, zinc-borosilicate, soda-lime-silica, lead-silicate, lead-zinc-borate glasses, however, any desired glass may be utilized. They may include phosphate glass systems having high coefficients of thermal expansion and relatively low temperature softening points. In addition, a vitreous or devitrified glass may be selected.

A preferred example of a useful glass which provides thermosetting properties suitable for application in an electronic environment is a devitrified, solder glass. This glass is a PbO—ZnO—$B_2O_3$ type glass and has a nominal composition of about 10 wt. % B, 0.025 wt. % A, 8.5 wt. % Si, 0.04 wt. % Ti, 0.01 wt. % Fe, 8.5 wt. % Zn, 12.5 wt. % Zr, 0.25 wt. % Hf, 2.0 wt. % Ba and the balance Pb. All elements are reported as wt. % of corresponding oxide. After the glass is liquid, it is held at a temperature of about 500° C. for about 10 minutes. The glass, upon solidification, then devitrifies. At that point, it will not remelt until it reaches a temperature of about 650° C. The glass is present in a range of from about 15 to about 50 volume percent of the fired composite and in a preferred range of from about 20 to about 40 volume percent. The glass is preferably selected with a softening temperature of from about 300° to about 1300° C. The processing temperature is selected so that the glass is at least above its softening point and preferably is in the liquid state.

A thermosetting composite may be formed by mixing the ceramic and metal particles with a glass that devitrifies above a certain temperature. First, the composite is preferably formed at a processing temperature where the glass is in a liquid condition. The composite may then be held in an oven at approximately the processing temperature for a sufficient period so that it has a devitrified structure when it solidifies. When the glass is in the crystalline state, it is usually much stronger than in the vitreous state. A composite of this nature, i.e. ceramic and metal particles mixed with a devitrified glass, may be characterized as a thermosetting material. The latter characteristic is imparted because the remelting temperature is considerably higher than the original processing temperature.

For example, a devitrifiable solder glass, CVIII manufactured by Owens Illinois Co., becomes liquid at a processing temperature of about 470° C. This glass as previously described is a PbO—ZnO—$B_2O_3$ type glass and has a nominal composition of about 10 wt. % B, 0.025 wt. % A, 8.5 wt. % Si, 0.04 wt. % Ti, 0.01 wt. % Fe, 8.5 wt. % Zn, 12.5 wt. % Zr, 0.25 wt. % Hf, 2.0 wt. % Ba and the balance Pb. All elements are reported as wt. % of corresponding oxide. After the glass is liquid, it is held at a temperature of about 500° C. for about 10 minutes so that upon solidification it has a devitrified structure. At that point, it will not remelt until it reaches a temperature of about 650° C. The thermosetting characteristics of the devitrified glasses are particularly advantageous because they allow the final product to be used in a higher temperature environment than the original processing temperature.

The third component of the composite comprises metallic particles which preferably are ductile at the processing temperature. The metallic particles are provided for their ability to reduce significantly the pressure necessary to densify the final composite product. It is believed that they mold about the surfaces of the ceramic particles when they are pressed between the ceramic particles during the processing procedures, thereby reducing or eliminating interlocking of the ceramic particles so as to reduce processing pressures. For example, the usual processing includes heating the mixture of ceramic particles with the metallic particles and the glass to the processing temperature where the metal particles are soft and ductile but not molten. The resulting composite slurry may be formed, i.e. in a mold. As the ceramic-glass-metal slurry flows into the shape of the mold, the ceramic particles are pressed against each other. The glassy phase is squeezed out from between adjacent ceramic particles providing points of contact. Without the presence of the metallic particles, the ceramic particles would remain in contact and could lock in position thereby retarding the ability of the slurry to flow. The ease of flowability is required for densification and shaping of the composite to the desired final configuration. Any loss of flowability becomes increasingly significant as the final shape becomes more complex.

A unique aspect of the present invention is the addition of metallic particles into the composite to significantly affect the flowability of the composite slurry. The metallic particles act sort of as a lubricant to enable the ceramic particles to slide over each other. It is believed that some of the metallic particles move into the interstices between adjacent ceramic particles and mold onto the ceramic particles at the points of contact which could interlock. It is believed that the metallic particles, being squeezed by the ceramic particles moving towards each other, adhere to the ceramic particles and then deform. This deformation enables the slurry containing the ceramic particles to move and flow, i.e. in a mold, while preventing damage to the ceramic particles.

The metallic particles may be constituted of any metal or alloy which does not melt at the processing temperature of the composite. Preferably, the metals and alloys are selected from the group consisting of aluminum, copper, iron, silver, gold, stainless steel and alloys thereof. Preferably, the selected metals and alloys are ductile at the processing temperature. Since any metal or alloy is ductile slightly below its melting temperature and below its solidus, respectively, a suitably selected processing temperature enables the use of any metal or alloy which will be ductile at the latter temperature. In the case where the metal or alloy is not ductile enough at the processing temperature, added pressure may be applied during the forming process to provide the required deformation. The metal or metal alloy particles preferably have an average diameter between about 0.01 to about 50 microns.

The final, fired composite may either contain the metallic particles dispersed continuously or discontinuously throughout the composite. Even in the case where the metallic particles are dispersed continuously, they do not form a matrix and are primarily subject to localized sintering. When the particles are dispersed continuously, the product would be classified as electrically conductive and when the particles are dispersed discontinuously the product would typically be classified as an insulator.

The metallic particles are present in the composite in an effective amount up to about 45 vol. % of the fired composite to enhance the flow characteristics of the composite at the processing temperature. Preferably, the metallic particles make up from about 5 to about 45 vol. % of the composite.

For applications where the composite is preferably classified as an insulator such as for electronic packaging components, the metallic particles are preferably provided in a volume percent so that they are discontinuously dispersed throughout the fired composite. Preferably, the metal or metal alloy particles in this instance make up less than about 25 volume percent of the final, fired composite. More preferably, the metal particles make up less than about 15 volume percent of the fired composite. Limiting the volume percent of metallic particles within these ranges is believed to prevent the formation of a continuous metal path in the final, fired composite.

The final composite, even with discontinuously dispersed metallic particles, exhibits improved thermal conductivity as compared with a composite formed with only ceramic particles bonded together with a glassy matrix. It is particularly surprising that the final composite having dispersed metallic particles has increased thermal conductivity since there is no corresponding increase in electrical conductivity. The reason for this unusual characteristic is not fully understood.

For application where the composite is preferably classified as electrically conductive, the metallic particles are preferably provided in a volume percent so that they are continuously dispersed throughout the fired composite. Preferably, the metal or metal alloy particles in this instance make up more than about 25 volume percent of the final, fired composite. More preferably, the metal or metal alloy particles make up from about 30 to about 45 volume percent of the fired composite. Limiting the volume percent of the metallic particles within these ranges is believed to promote the formation of a continuous metal path in the final, fired composite thereby providing good electrical conductivity as well as thermal conductivity. Such an electrically conductive composite is believed to have wide application in areas outside the electronic packaging field such as in engineered composites and electronic composites where electrical conductivity is desired.

The process of forming the composite of the present invention includes providing three primary components; ceramic particles, metallic particles and a glass. The process may be accomplished by different techniques depending on the specific materials selected. For example, the ceramic particles may first be mixed with relatively ductile metal particles. Next, glass particles for bonding the ceramic particles together are added to the mixture. The mixture is heated to the processing temperature preferably corresponding to the temperature at which the glass particles are liquid and at least to their softening temperature. This preferably provides a semi-solid slurry of molten glass with solid metal and ceramic particles dispersed therein. Then, the composite preferably as a semi-solid slurry can be formed by conventional processes such as hot forging or hot pressing in a mold to any desired shape. With hot pressing, the mixture is preferably compacted at a pressure of from about 500 pounds per square inch (psi) to about $300 \times 10^3$ psi. The lowest usable pressure is believed to be that which enables the metallic particles, adhered between adjacent ceramic particles, to deform. This depends on the ductility of the metal or alloy at the processing temperature. In the event that the metal is not ductile enough at the processing temperature, a higher pressure may be used to deform the metal particles.

Finally, the mixture is cooled to solidify the glass and bind the composite into a final devitrified shape. A conventional parting agent, such as boron nitride, may be provided on the mold walls to enhance the removal of the pressed product from the mold. Preferably, the parting agent does not stick to either the mold walls or the pressed body. However, the primary consideration is that the parting agent does not stick to the mold walls. An important advantage of the present invention is that the pressed composite is very dense and has a final shape that very closely corresponds to that of the mold.

The present invention can produce parts with much tighter tolerance, and a more complex shape than ceramic manufacturing processes currently available in the industry. This significant advantage is primarily due to the following reasons. Firstly, the starting materials do not necessarily contain any constituents, such as organics, which are lost during the actual process of fabrication. These losses can result in undue shrinkage. Secondly, the metal particles enable the ceramic particles to better flow over each other during processing. Another important advantage is that the firing temperature may be substantially lower than the range of temperatures at which ceramic materials are now fired. Processing at a lower temperature inherently decreases the processing cost as compared to any known process.

The fabrication process may include conventional steps including hot pressing and hot forging. Hot pressing can be carried out directly on the mixture of powders or on cold compacts. Depending on the glass, however, the hot pressing may require oxidizing atmospheres. For example, a solder glass such as $PbO-ZnO-B_2O_3$ requires an oxidizing atmosphere to prevent a change in the state of the glass.

Additional improvements in both thermal and mechanical properties can be obtained by using devitrified glasses in the composite. For electronic packaging, a devitrified glass enables the package to be formed at a significantly lower temperature than the temperature at which the package can operate.

An exemplary process follows.

About 45 vol. % of a devitrifying glass (Owens Illinois CVIII) in fine particulate form (−325, 90% mesh) was mixed with about 45 vol. % of fine particulate $Al_2O_3$ (−120 mesh) and about 10 vol. % of fine atomized aluminum metal powder (−325 mesh). The resulting mixture was cold compacted at about $50 \times 10^3$ psi. The cold compacts were then hot pressed into $1\frac{1}{4}''$ dia. 0.1" thick discs at a temperature of about 470° C. and under a pressure of about $25 \times 10^3$ psi. The discs were then placed in an oven and kept at a temperature of about 500° C. for about 10 minutes so that the final structure was devitrified.

An example of a ceramic-glass-metal composite formed of a vitreous glass follows.

About 45 vol. % of a vitreous glass (Corning 7052) in a fine particulate form (−325, 90% mesh) can be mixed with about 45 vol. % of fine particulate $Al_2O_3$ (−120 mesh) and about 10 vol. % of fine atomized iron metal powder (−325 mesh). The resulting mixture can be cold compacted at about $50 \times 10^3$ psi. The cold compacts can then be hot pressed into disks at a temperature of about 1220° C. and under a pressure of about $25 \times 10^3$ psi pressure. The disc can then be solidified into a final structure that is vitreous. The resultant disc are thought to be very dense, and have a thermal expansion of about $70 \times 10^{-7}$ in./in./°C.

Figure 2:
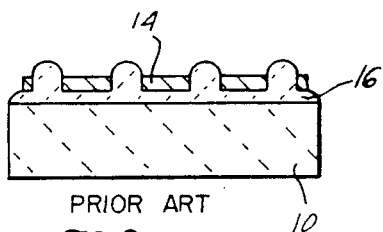
FIG. 2 illustrates a prior art substrate having a leadframe glass bonded thereto.

The composite described hereinbefore is particularly suitable for applications relating to semiconductor packaging. A first preferred embodiment is directed to a CERDIP package wherein the unique composite of the present invention is substituted for the ceramic base and lid of the prior art as illustrated in FIG. 1. The prior art package 8 typically included a ceramic base 10 and lid 12 with a leadframe 14 disposed therebetween. The leadframe is first bonded with a sealing glass 16 to the base component 10. The glass 16 bonding the leadframe to substrate 10 protrudes above the upper surface of the leadframe as illustrated in FIG. 2. Then, the device 18 is bonded to the surface of the base using a conventional sealing material. Next, the device is electrically connected to the leads with bonding wires 20. A preform 21 of the sealing glass may be disposed between the leadframe and the lid 12. Finally, the lid 12 is stacked on the glass preform and the base 10. The structure is then subjected to a temperature and pressure to hermetically seal the package. A potential weakness of the prior art CERDIP packages becomes evident in FIG. 1. The sealing glass disposed between the base and lid, has the leadframe embedded therein. Therefore, the glass and the glass bonding sites, on either side of the leadframe, are subject to high stress from flexure of the leadframe. The leadframe is usually subjected to this type of flexure during the handling and installation of the package.

With the advent of the ceramic-glass-metal composite of this invention, ceramic shapes can be formed at relatively low temperatures, i.e. below about 500° C. This is particularly useful in fabricating semiconductor packages where, because of the tremendous volume cost savings is a critical issue. Since a low temperature can be used to form the ceramic-glass-metal composite, the mold has a longer working life and lower energy requirements are needed. However, a vitreous, low temperature glass for the glassy phase may result in the formed composite being subject to deterioration from exposure to high operating temperatures. The solution to this potential problem may be to form the glassy matrix from a devitrified glass as explained hereinbefore.

An important aspect of the present invention is the ability to embed metallic elements into the composite. This can be accomplished in a single step during the forming of the composite into a final shape. The metallic element is preferably formed of any metal or alloy which is thermally compatible with the glassy phase in the composite. If the metallic element does not adhere to the glassy phase, it may be appropriate to place an adherent coating on the surface of the metallic element to accomplish the same purpose. Examples of suitable metals include the group consisting of nickel, copper, aluminum, iron, gold, silver and alloys thereof.

Applying this technology to the fabrication of electronic packaging results in strong, inexpensive, rapidly manufactured packages which can have a large number of configurations. For example, this technique may be utilized to embed a leadframe into a substrate during the hot forming step in the manufacture of a CERDIP. The result is a leadframe embedded directly into the ceramic-glass-metal composite, rather than into the glass sealant as in a conventional CERDIP. This new structure eliminates one of the significant weaknesses of the CERDIP structure, i.e. the breaking of the glass seal fom leadframe flexure.

Figure 3A:
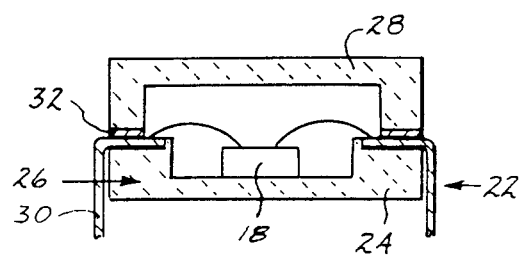
FIG. 3A illustrates a CERDIP package in accordance with the present invention.

Referring to FIG. 3, there is illustrated a semiconductor casing 22. The base component 24 and lid component 28 are both formed of a ceramic-glass-metal composite material 26 of this invention. The composite material comprises ceramic particles, a glassy phase for adhering the ceramic particles together, and metallic particles dispersed discontinuously throughout the composite. A metallic leadframe 30 is embedded into the base component 24. A sealing glass 32, such as a solder glass from the group consisting of borosilicate, soda-lime-silica, lead-silicate and lead-zinc-borate, bonds the base component 24 to the lid component 28.

The ceramic-glass-metal composite material 26 may be constituted in accordance with the principles set forth earlier in this specification. For example, the ceramic particles comprise about 20 to about 80 vol. percent of the final composite and preferably about 40 to about 65 vol. percent of the composite. The ceramic particles are selected in a range of from about 1 to about 200 microns in size. The metal particles comprise an effective amount up to about 25 vol. percent and preferably an effective amount up to about 15 vol. percent of the composite for enhancing the flow characteristics of the composite at the processing temperature. The latter temperature is selected to preferably be above the glass softening temperature of the glass, which bonds the composite together, and more preferably at or above the temperture at which the glass becomes liquid. Moreover, the bonding time and temperature of the sealing glass 32 is selected so that the glass in the composite does not become soft enough for the lid and base to significantly deform. In addition the metallic particles are about 0.01 to about 50 microns in size. The metallic particles have a melting temperature above the processing temperature which has been selected for enhancing the flow characteristics of said composite. The metallic particles are selected so as not to be molten at the processing temperature for forming the composite. The glass for adhering the composite together is selected from the group consisting of vitreous and devitrified glass.

By using devitrified glasses as the matrix of the composite, additional improvement in thermal and mechanical properties of the CERDIP package disclosed herein can be obtained. Specifically, devitrified glass results in improved thermal conductivity and mechanical properties of the composites.

A semiconductor casing 22, as illustrated in FIG. 3, may be fabricated with the following steps. A base component 24 and a lid component 28 can be manufactured by first cold compacting the ceramic-glass-metal mixture with an organic binder, such as polymethylmetacrylate (PMMA) and polyvinylalcohol (PVA), to the appropriate dimensions and shapes. The components can then be fired to a temperature of less than about 400° C. to burn off the organic binder. Then, as illustrated in FIG. 3B, a metallic leadframe 30 is placed on the top surface of the base component and hot pressed at a temperature where the glass is soft and at a pressure up to about $300 \times 10^3$ psi so that the top surface of the leadframe remains exposed and the glass consolidates and fills in the voids left by the burning out of the organics. The leadframe is preferably formed of any metal or alloy which is thermally compatible with the glassy phase in the composite. Also, the leadframe material is preferably bondable to the glassy phase of the composite as well as the sealing glass 32. If the metallic leadframe itself does not adhere to the glassy phase, it may be appropriate to place an adherent coating on the surface of the metallic leadframe to accomplish the same purpose. Examples of suitable leadframe metals include nickel, copper, aluminum, iron, gold, silver and alloys thereof. However, the present invention is not limited to these metals or alloys and includes any metal or alloy which will function as required. Typically, a semiconductor device 34 may be attached to the base component using a conventional bonding material, such as, gold-silicon attach alloys or solder. Next, the device 34 may be wire bonded to the ends of the leadframe. Then a preform of sealing glass 32 may be disposed between the base component 24 and the lid component 28. The package is then heated to the softening temperature of sealing glass 32 and pressed together. Next, the package is cooled to solidify the sealing glass 32 and form a hermetic seal.

The semiconductor casing of the type illustrated in FIG. 3 has unique advantages over the the prior art CERDIP's. For example, the pressing of the leadframe into in the base component will result in significantly better lead coplanarity. This may improve the speed of ultrasonic wire bonders since the bonding operation of the lead wires between the leadframe and the chips may be significantly faster. Also, the shiny glass between the lead tips as shown in FIG. 2, has been substantially eliminated. This is because the leadframe 30 is now affixed into the ceramic-glass-metal base component 24 as illustrated in FIG. 3B. The advantage is a significant increase in the efficiency of the vision recognition system and a corresponding increase in the productivity of the wire bonding operation. Currently, vision recognition systems are utilized to automatically locate the lead tips of the leadframe attached to the CERDIP part. The systems often mistake the intervening glass for the lead tip as the reflectivity of the glass is equal to or better than the aluminum on the lead tip. Since the vision recognition system operates on a gray scale of contrast, the problem causes serious malfunctioning of the vision recognition systems. The current solution is to keep the glass at a much lower level as compared to the lead tips. This may be accomplished by tighter process control but often recognition error remains and the rejected work has to be completed in a manual machine. The present process can provide a dark ceramic, adjacent the aluminized or metallized lead, which provides excellent contrast.

Figure 4:
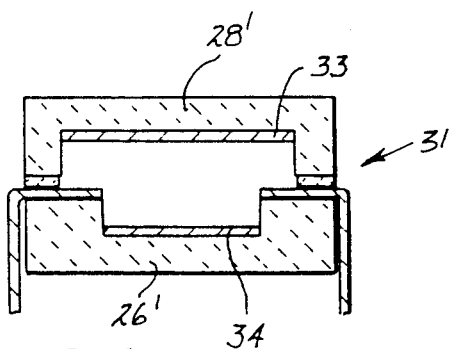
FIG. 4 illustrates a CERDIP package having metal coupons in the base and lid cavities in accordance with the present invention.

Referring to FIG. 4, there is illustrated another embodiment of an electronic package 31 which includes metallic plates 33 and 34 embedded in the inside cavities of the lid and base components 28' and 26', respectively. This package 31 may be manufactured in a similar manner to that described above with reference to the embodiment illustrated in FIG. 3. The components illustrated in FIG. 4 which are essentially the same as those illustrated in FIG. 3 have the same reference numeral with a prime. The metallic plates reduce the "soft error" probability as the metallic materials usually contain a significantly lower quantity of naturally present radioactive elements as compared to conventional ceramics. Radioactive elements are responsible for soft errors which are a significant problem for semiconductor memories. Conventional ceramic manufacturers resort to expensive materials to reduce the radioactivity of the ceramic parts. The present invention overcomes this problem by embedding a metallic plate 33 into the cavity of the ceramic composite lid 28' as shown in FIG. 4. This metallic plate is preferably formed of any metal or alloy which is thermally compatible with the glass matrix of the composite. Also, the metallic material is preferably bondable to the glassy phase of the composite. If the metal itself does not adhere to the glassy phase, it may be appropriate to place an adherent coating, such as a plating on the surface of the metal to accomplish the same purpose. Examples of suitable metallic material includes nickel, copper, aluminum, iron, gold, silver and alloys thereof. It is also within the terms of the present invention to place a metallic plate 34 in the cavity of the base plate, which in conjunction with the metallic plate 33 in the lid, will provide electromagnetic shielding. The metallic plate disposed in the cavity of the base has the same selection requirements as specified for the plate in the lid.

The CERDIP parts, manufactured with metal plates, have an additional advantage as compared to parts produced by conventional methods. The die attach cavity metallization may be accomplished by electroplating a much smaller thickness as compared to the conventional method of thick film application in the die cavity. In a conventional thick film application method, a thickness of as high as about 600 to about 700 micro-inches of gold is applied. This thickness results from the sintering process The fired gold layer has a porosity as a result of the sintering process. The gold paste contains as its main ingredients powders of gold and glass. These powders are contained in an organic base consisting of a solute phase and a solvent phase to provide the appropriate rheology for the application of paste. The porous nature of the sintered gold also necessitates thicker layers to safeguard against process problems at die attach, i.e. the unknown extent of porosity is and cannot be properly controlled. During the firing process, the glassy flux chemically bonds with the substrate. The bond between the glass and the gold, however, is mechanical in nature. The glassy phase and gold interweave and form numerous mechanical locks. The extra amount of gold used to form such a bond is special for this application and not necessary in electroplating gold to a metal plate.

The electroplated layer of gold on the metallic plate or coupon, i.e. base plate 34, need not be any thicker than about 50 to about 60 micro-inches to accomplish the same objective. As gold constitutes a significant portion of the cost of a CERDIP, i.e. about 40%, a reduction in gold usage by as much as 90% would dramatically reduce the cost of the part.

The present invention is not limited to CERDIP's but also includes other design configurations, such as CERQUADS. This is similar to a CERDIP except that the leads extend from all four sides of the package. In the past this was not feasible with ceramic packages because of the impact of the lead flexure on the seal.

Figure 5:
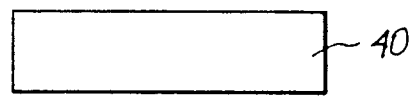
FIG. 5 illustrates a substrate of the ceramic-glass-metal composite in accordance with the present invention.
Figure 6A:
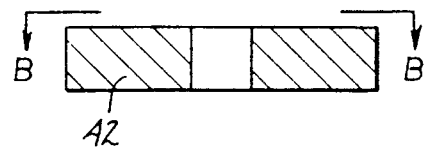
FIG. 6A illustrates a layer of the ceramic-glass-metal composite with an opening extending therethrough.
Figure 7A:
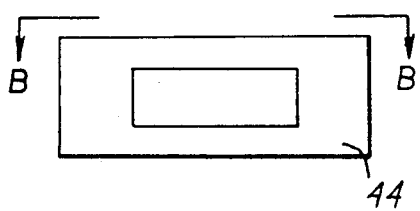
FIG. 7A illustrates a layer of the ceramic-glass-metal composite with an opening extending therethrough.
Figure 6B:
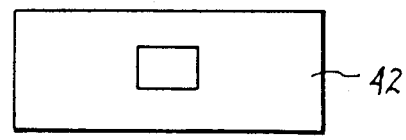
FIG. 6B is a view through section B—B of FIG. 6A.
Figure 7B:
FIG. 7B is a view through section B—B of FIG. 7A.

Another embodiment of the present invention is directed to the production of multi-layer packages as shown in FIGS. 5 through 10. In FIG. 5 a first layer of cold pressed ceramic-glass-metal composite 40, in accordance with the principles described hereinbefore, is illustrated. In FIGS. 6A and 6B, a second layer of cold pressed ceramic-glass-metal composite 42, preferably of the same material as used to form layer 40, is illustrated. In FIGS. 7A and 7B, a third layer of cold pressed ceramic-glass-metal composite 44, preferably of the same material as used to form layer 42, is illustrated.

Metallic elements in various configurations as desired may be added at different locations and assembled in accordance with the specific requirements of the component being fabricated. For example, in FIG. 8 a leadframe component 46 is disposed about layers 40' and 42'. Components which are essentially the same as those illustrated in another Figure have the same reference numeral primed. Also, a metallic element 48 is placed on the surface of the first layer 40'. Further a metallic seal ring 50 is placed on the top surface of the third layer 44'.

The structure 49, formed by these ceramic-glass-metal components in conjunction with the metallic elements 48 and 50, is then hot pressed to embed the leadframe 46 and the seal ring 50 into the composite bodies 47 to form the structure 54 illustrated in FIG. 9. This FIG. 9 is not to the same scale as FIG. 8. The hot pressing may be done at a processing temperature dependent upon the selection of the glass for the glassy matrix of the composite. The metallic element 49 may be electroplated with a layer of gold to enhance the bonding of a semiconductor die thereto. The die may be attached within the cavity and wire bonded to the ends of the leads 51. Finally, a metallic cover (not shown) can be sealed to the seal ring 50.

The metal used in forming the hermetically sealed component, or any other similar device, may be surface coated in a variety of ways. For example, the metal may be gold plated. A typical processsing temperature of about 470° C. for borosilicate solder glasses would not degrade the quality of such a plating. Also, the metal could be selectively plated, e.g., the bond tips 31 and the exposed portions of the leadframe can be gold plated. The metal area in contact with the composite may be nickel plated to improve the adhesion between the glass and the metal. Portions of the metal inserts 48 or 50 could be plated after embedding into the composite. It is also within the terms of the present invention to plate with any desired metal or metal alloy as required by the specific requirements of the material system and the application of the product. Further, composite metal inserts 48 or 50 wherein the cladding is the desired coating can be used if appropriate.

Referring to the embodiment illustrated in the FIG. 10, there is shown a package 59 which is similar to the CERDIP type package of FIG. 9 with the addition of a heat sink 60 and a top cover 62. The package 59 may be classified as a leadless ceramic chip carrier. This embodiment takes advantage of the ability to bond a metal structure into the composite. The metal structure is selected in accordance with the principles discussed regarding the metallic elements 33 and 34 of FIG. 4. The heat sink 60 has an upper section 68 having a peripheral shape being substantially the same as cavity 65 in the composite body 66 and extending into cavity 65. The heat sink 60 also has a lower section 69, larger than the upper section 68 which extends to an outer surface 67 of the composite body 66. The heat sink 60 has the dual function of removing heat generated by die 63 and providing a surface 61 to which the die 63 can be bonded. Again the surface 61 can be gold plated as discussed hereinbefore. The top cover 62, may be fabricated of any desired metal or alloy, such as those selected for the leadframe 46, and can be bonded to the seal ring 50' using conventional techniques such as soldering and brazing.

Referring to the embodiment of FIG. 11, there is shown a package 70, similar to that of FIG. 10, except that the external leads 72 are brazed or welded to the leadframe 73 embedded in the ceramic body 74. The added fins 71 on the heat sink 60' are optional. Moreover, the metal heat sink 60' itself is optional and provided to improve thermal performance although it may be omitted, if desired. The heat sink 60' is preferably formed of a high conductivity metal or alloy, such as, for example, one being selected from the group consisting of copper, aluminum, gold, silver, nickel, iron and alloys thereof, which is compatible with the ceramic-glass-metal composite material used to form the ceramic body 74. The metal lid 62' is preferably soldered, brazed or welded to the metal seal ring 50" embedded in the composite body 74.

Referring to the embodiment illustrated in FIG. 12, there is shown a package 80 which is similar to the package 59 of FIG. 10. The difference between package 59 and package 80 resides in the seal ring 50' and metal cap 62 having been replaced with a ceramic-glass-metal composite cover 82 and a sealing glass 84. Again, the heat sink 60" is optional and may be omitted, if desired. The embedded internal leads 88 may, if desired, be fabricated from a material of relatively low thermal conductivity since the lead and leadframe do not provide a significant contribution to the thermal performance. The leads 90 may also be fabricated from a relatively low conductivity material. Since both the leadframe 88 and the leads 90 are formed from a solid metal, the leads 90 may be attached to the leadframe 88 by spot welding rather than gold alloy brazing to gold metallization as is typically done in the multilayer packages. This may provide a significant cost advantage.

Referring to the embodiment of FIG. 13, there is illustrated a package 100 which provides a high quality replacement for a CERDIP package. The ceramic-glass-metal component 102 forms the body of the package. A leadframe 104 is embedded in the body 102. Leads 90' may be affixed to the leadframe 88' by any conventional technique such as brazing or by spot welding. A metal seal ring 50''' is also embedded into the top surface 110 of the component 102. The seal ring 50''' has a gold coating 112 disposed on its upper surface. Also, a gold coating 114 is provided on the ends of leadframe 88' to enhance the bonding of bonding wires from a chip. Finally, a conventional lid 62''' is provided to be sealed to the seal ring by any conventional means such as soldering.

Referring to the embodiment of FIG. 14, there is illustrated a package 120 which is similar to that illustrated in FIG. 13. However, to reduce the cost of the package, the metal top 62''' and gold coating 112 are replaced with a ceramic lid 82' bonded directly to a ceramic-glass-metal component 102' with a solder glass 84'.

Referring to the embodiment of FIG. 15, there is illustrated a package or semiconductor casing 130 which is provided with a unique heat sink that has superior thermal performance. The package 130 includes a body component 131 having a cavity 133 adapted to receive a semiconductor device 135. A leadframe 134 is also embedded into the body component 131 with lead ends 139 extending into the cavity for wire bonding to the semiconductor device 135. A cup shaped component 132 is molded into the ceramic-glass-metal component 131 so that the surface 137 of the cup becomes the die mounting surface. A flange 136, extending substantially perpendicular from sidewalls 142 of the component 132, becomes a portion of the bottom surface of the casing 130. In effect, the flange 136 becomes a heat sink. The flange 136 may also include folded up end sections 138 which extend substantially perpendicular to the flange 136 and up the sides of the package. However, it is within the terms of the present invention to delete the end sections 138. If desired, a metallic element 140, such as a high conductivity material like copper, may be affixed to the bottom of the package to bridge from one portion of the flange 136 to the other portion of the flange and further improve the heat sink capabilities of the flange. Also, the sidewall 142 of the drawn section of the cup 132 may be provided with a plurality of ports 144 through which the ceramic-glass-metal mixture flows in order to fill the cavity. To provide maximum thermal performance, the flange cup is preferably selected of a high thermal conductivity material, such as copper. The thickness of the cup may be maximized without failure of the bond between the ceramic-glass-metal composite and the metallic cup due to mismatch in the coefficients of thermal expansion. A sealing lid, not shown, may be attached onto the top surface 146. The lid may be formed of any desired material such as metal, glazed metal or a ceramic and bonded in accordance with the techniques described with regards to the embodiments illustrated in FIGS. 12, 13 and 14, i.e. with a sealing glass, with a seal ring and a gold-tin solder or with a solder glass.

Figure 16A:
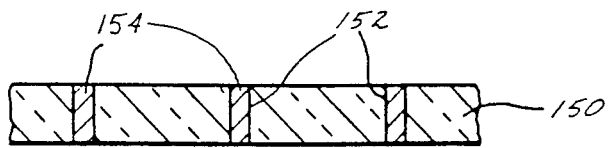
FIGS. 16A–16E illustrate the series of steps for forming a multilayer, ceramic-glass-metal circuit structure in accordance with the present invention.

The ceramic-glass-metal composites, as described herein, are particularly useful to fabricate multi-layer, ceramic-glass-metal substrates which can contain electrical conductor patterns between adjacent pairs of a plurality of ceramic-glass-metal substrates. The manufacturing steps of a typical unit will now be described. The assembly begins with a substrate 150, as illustrated in FIG. 16A, preferably formed by the process of consolidating a mixture of the ceramic-glass-metal composite with a organic binder, such as PMMA. Note that any number of through-holes 152 are provided as required. These through-holes 152 are of any desired diameter and are typically in the range of about 5 to 20 mils. The size of the through-holes 152 does not make up part of the invention and they may be larger or smaller as required. The holes 152 may be filled with a conductor 154, such as a conductive paste of an organic carrier and particles of any desired conductive material, such as, for example, gold, silver, platinum, palladium, copper and alloys thereof. If desired, the glass used in the substrate 150 may be mixed with the conductor particles in order to increase the bond strength between the conductor 154 and the ceramic-glass-metal substrate 150. The through-holes may also contain a solid wire or be filled with a conductor such as solder. The layers of metal 156, 158 may be formed of any desirable conductive material, such as, for example, copper, aluminum, iron, copper-silver, copper-gold and alloys thereof.

Figure 16B:
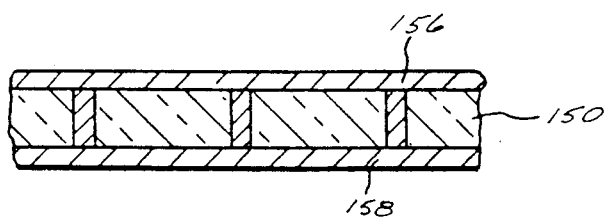

Referring again to FIG. 16B, layers 156 and 158 of metal foil may be disposed on one or both surfaces of the ceramic-glass-metal structure 150. Preferably, the layers 156, 158 of metal foil adhere to the glass in the ceramic-glass-metal substrates. However, it is within the terms of the present invention to bond the layers of foil to the substrate with a glass as disclosed in U.S. Pat. No. 4,725,333. For example, the metal foil may be selected from the group consisting of deoxidized copper alloy and oxygen free copper alloy; the glass may be selected from the group consisting of silicate, borosilicate, borate, and phosphate glasses. The structure 150 is first fired to a temperature which burns out the organic binders. This burn out temperature is typically less than about 400° C., although it may be higher, if appropriate. The stacked assembly of foil and ceramic-glass-metal substrate are then heated to the glass softening temperature and subjected to a lamination pressure so that the layers of metal foil adhere to the glass matrix within the substrate 150 and the conductor 154 in the through-holes 152 contacts the layers of foil 156 and 158. It is also within the terms of the present invention to dispose a layer of glass between the substrate 150 and the layers of foil 156, 158. The structure is heated to a temperature where the layers of glass soften and bind the layers of foil 156, 158 to the substrate 150.

Figure 16C:
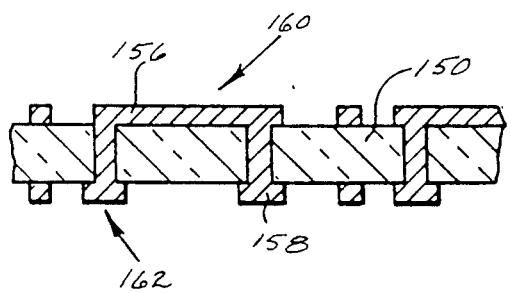

Referring to FIG. 16C, multilayered circuit patterns 160, 162 may be formed in the foil layers 156, 158 by any desired process such as etching with conventional dry film, photoresist techniques. Using conventional photo-etching techniques includes coating the outer surfaces of foil layers 156 and 158 with a conventional positive photoresist which may consist of a light sensitive resin of the photodegradable type. Then, a prescribed patterned mask of material, opaque to exposing light, is placed in contact with the photoresist. On light exposure, only the unmasked portion of the photoresist layer gets exposed. The mask is then removed and the resist is developed. The exposed portions of the resist are removed and the circuitry formed in a subsequent etching process. The etching may be accomplished with any conventional solution such as potassium iodide or a $FeCl_3/HCl$ copper etchant. The assembly may be coated with photoresist and etched in this manner several times to produce the desired patterns and structures. This assembly may be adapted to be a hybrid circuit device.

Figure 16D:
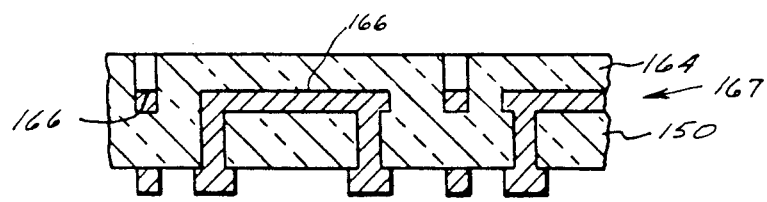

Then, as shown in FIG. 16D, a second ceramic-glass-metal structure 164 which may be formed by the same process as structure 150, as described hereinbefore, is disposed or stacked on the top surface 166 of the foil bonded to structure 150. The assembly is heated to a temperature where the glass in each of the substrates 150 and 164 softens. Then, a lamination pressure may be applied to press the structure 150 against the structure 164 to cause adhesion between the glass of the two structures. A pressure of less than about 300 psi is thought to be adequate to carry out this step. However, any appropriate lamination pressure may be applied.

Although the invention has thus far been described with the electrical patterns being cut into the foil subsequent to the adherence to the substrate 150, it is also within the terms of the present invention to form the electrical conductor patterns in the foil by any desired technique prior to applying the foil to the substrate. Then, the substrate and foil may be heated to the glass softening temperature and placed under lamination pressure so that the foil adheres to the ceramic-glass-metal substrate as shown in FIG. 16C.

Thereafter, the steps described above to produce a multilayer hybrid circuit assembly 167 as seen in FIG. 16D, may be repeated to form any number of layers. The resulting structure 167 is particularly advantageous in that it is not substantially affected by thermal contraction typically experienced by the ceramic-glass-metal structures as they cool from the consolidation temperature to room temperature. The resulting hybrid circuit assembly is, therefore, reproducible and the circuitry between the conductor layers and the electrical interconnects maintain through-hole contact. For example, the conductors in through-holes 170 and 172 of structure 164 make contact with the circuitry 160 formed on the ceramic-glass-metal structure 150.

Referring again to FIG. 16E, there is shown an additional substrate 178 which includes a plurality of conductor filled through-holes 180 in contact with the conductive circuitry on the surface 182 of substrate 150. The alignment of the through-holes 180 with the conductive circuitry 162 can be controlled to substantially eliminate problems with through-hole electrical contact. Finally, conductor pins 184 may be attached by any means, such as brazing, to the conductor filled through-holes 180 to form a pin grid array structure 168.

In another embodiment of the present invention, the circuitry 160 and 162 as illustrated in FIG. 16C, may be applied to the substrate 150, as shown in FIG. 16A, by screen printing a metal conductor paste onto the substrate 150. With this process, the substrate 150 may be formed with a high temperature glass and fired prior to the application of the conductor paste. Then, the conductor paste is preferably pressure sintered up to about $300 \times 10^3$ psi at a temperature of from about 450° to about 1000° C. to consolidate the metallic particles in the printed conductors so that they become highly conductive as well as being bonded to the glass in the ceramic-glass-metal substrate 150. This step may be accomplished within a mold in order that the substrate does not lose its desired shape.

Figure 16E:
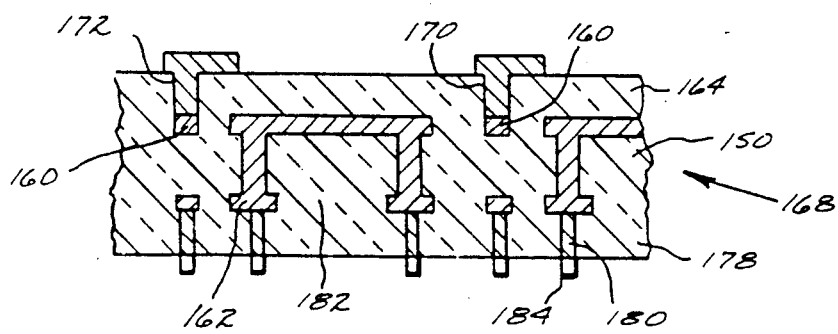

Thereafter, additional substrates may be disposed on either side of substrate 150, as shown in FIGS. 16D and 16E, so as to form a multilayer structure similar to 167 and 168 described hereinbefore.

For the purpose of this invention, a final, fired composite is defined as the composite after densification at the processing temperature. Discontinuously dispersed means that the particles are not generally interconnected so as to provide electrical conductivity. Continuously dispersed means that the particles are generally interconnected to provide electrical conductivity.

The terminology "thermally compatible", as used within the specification, defines materials having coefficients of thermal expansion which are relatively close to one another.

Each of the packages or substrates described in connection with this invention may be constructed by initially cold compacting a mixture of the ceramic-glass-metal particles with organic binders into a preform. Then, the preform can be heated to volatilize and drive off the binders. Next, the preform may be hot formed into the final desired shape.

Although this case has been described in terms of hot forming under pressure, it is also within the terms of the present invention to form the ceramic-glass-metal slurry by any glass forming method such as casting, blowing, blow molding, etc.

The patent and patent applications set forth in this application are intended to be incorporated in their entireties by reference herein.

It is apparent that there has been provided in accordance with this invention electronic packaging of components incorporating a ceramic-glass-metal composite which satisfies the objects, means and advantages set forth hereinabove. While the invention has been described in combination with the embodiments thereof, it is evident that many alternatives, modifications, and variations will be apparent to those skilled in the art in light of the foregoing description. Accordingly, it is intended to embrace all such alternatives, modifications and all variations as fall within the spirit and broad scope of the appended claims.

We claim:

1. A composite combined with a metallic component, comprising:
   a base component formed of a ceramic-glass-metal composite material;
   said composite material comprising an effective amount up to about 25 volume % of metallic particles for enhancing the flow characteristics of said composite;
   from about 15 to about 50 volume % of a glass for adhering said composite together; and
   the balance essentially ceramic particles wherein said glass reacts chemically with both said metallic particles and said ceramic particles and said metallic particles have a melting temperature greater than the melting temperature of said glass;
   said composite having a structure comprising substantially a matrix of said glass with said ceramic and metallic particles dispersed therein; and
   a metallic component, said component being embedded into said composite material.

2. The composite of claim 1 including said ceramic particles comprising from about 20 to about 80 vol. percent of said composite; and
   said ceramic particles being from about 1 to about 200 microns in size.

3. The composite of claim 2 further including the glass matrix being from the group consisting of vitreous and devitrified glass.

4. The composite of claim 2 including said glass matrix being selected from the group consisting of silicate, borosilicate, phosphate, zinc-borosilicate, soda-lime-silica, lead-silicate and lead-zinc-borate glasses.

5. The composite of claim 3 including said metallic particles being discontinuously dispersed throughout said composite.

6. The composite of claim 5 including said metallic particles comprising at least about 5 volume % of said composite and being from about 0.01 to about 50 microns in average diameter.

7. The composite of claim 3 wherein said metallic component is a material selected from the group consisting of nickel, copper, aluminum, iron, gold, silver and alloys thereof.

8. The process of fabricating a composite combined with a metallic component, comprising the steps of:
   providing a base component formed of a ceramic-glass-metal composite material, said composite material comprising an effective amount up to about 25 volume % of metallic particles for enhancing the flow characteristics of said composite;
   from about 15 to about 50 volume % of a glass for adhering said composite together; and
   the balance essentially ceramic particles wherein said glass reacts chemically with both said metallic particles and said ceramic particles and said metallic particles have a melting temperature greater than the melting temperature of said glass;
   said composite having a structure comprising substantially a matrix of said glass with said ceramic and metallic particles dispersed therein;
   providing a metallic component; and
   embedding said metallic component into said composite material.

9. The process of claim 8 further including the step of including said ceramic particles to comprise from about 20 to about 80 vol. percent of said composite, and said ceramic particles being from about 1 to about 200 microns in average diameter.

10. The process of claim 9 further including the step of selecting the glass matrix from the group consisting of vitreous and devitrified glass.

11. The process of claim 10 further including the step of selecting said metallic particles to comprise at least about 5 volume % of said campsite and to be from about 0.01 to about 50 microns in average diameter and discontinuously dispersed throughout said composite.

12. The process of claim 10 wherein said metallic component is a material selected from the group consisting of nickel, copper, aluminum, iron, gold, silver and alloys thereof.

13. The process of forming a semiconductor casing, comprising the steps of:
   providing a first component and a second component each formed of a ceramic-glass-metal composite material;
   said composite material having a structure comprising substantially a matrix of said glass with said ceramic and metallic particles dispersed therein wherein said glass reacts chemically with both said metallic particles and said ceramic particles and said metallic particles have a melting temperature greater than the melting temperature of said glass;
   providing a metallic leadframe;
   embedding said leadframe into said first component;
   disposing a sealing glass between said first component and said second component;
   heating said second component, said base component and said sealing glass to a temperature where said sealing glass is in the liquid state;
   pressing said first and second components together; and
   solidifying said sealing glass to bond said first component to said second component.

14. The process of claim 13 wherein said first component comprises a base and said second component comprises a lid.

15. The process of claim 14 including the step of selecting said ceramic particles to comprise from about 20 to about 80 vol. percent of said composite.

16. The process of claim 15 including the step of selecting said ceramic particles between from about 1 to about 200 microns in average diameter.

17. The process of claim 16 including the step of selected said ceramic particles from the group consisting of $Al_2O_3$, SiC, BeO, $TiO_2$, $ZrO_2$, MgO, AlN, $Si_3N_4$, BN and mixtures thereof.

18. The process of claim 17 including the step of selecting said metallic particles to comprise an effective amount up to about 25 vol. percent of said composite, said metal particles being discontinuously dispersed through said composite.

19. The process of claim 18 including the step of selecting said metallic particles to comprise at least about 5 volume % of said composite and to be from about 0.02 to about 50 microns in average diameter.

20. The process of claim 19 including the step of selected said metallic particles from the group consisting of aluminum, copper, iron, silver, gold, stainless steel and alloys thereof.

21. The process of claim 19 further including the step of selecting the glass for adhering said composite from the group consisting of vitreous and devitried glass.

22. The process of claim 19 further including the step of selecting said glass matrix from the group consisting of silicate, borosilicate, phosphate, zinc-borosilicate, soda-lime-silica, lead-silicate and lead-zinc-borate glasses.

* * * * *

UNITED STATES PATENT AND TRADEMARK OFFICE
CERTIFICATE OF CORRECTION

PATENT NO. : 5,024,883

DATED : June 18, 1991

INVENTOR(S) : Narendra N. Singhdeo et al

It is certified that error appears in the above—identified patent and that said Letters Patent is hereby corrected as shown below:

At column 20, line 68, please delete "campsite" and insert ---composite--- in its place.

Signed and Sealed this

Twenty-third Day of February, 1993

Attest:

STEPHEN G. KUNIN

*Attesting Officer*      *Acting Commissioner of Patents and Trademarks*